United States Patent [19]

Simon et al.

[11] Patent Number: 5,513,660
[45] Date of Patent: May 7, 1996

[54] EXPANDABLE URETHRAL PLUG

[75] Inventors: John G. Simon, Boston; Paul D. McLaughlin, Scituate, both of Mass.; Leo C. Felice, Pascoage, R.I.

[73] Assignee: UroMed Corporation, Watertown, Mass.

[21] Appl. No.: 424,585

[22] Filed: Apr. 18, 1995

Related U.S. Application Data

[63] Continuation of Ser. No. 88,469, Jul. 7, 1993, abandoned, which is a continuation-in-part of Ser. No. 811,571, Dec. 20, 1991, which is a continuation-in-part of Ser. No. 746,364, Aug. 16, 1991, abandoned, which is a continuation-in-part of Ser. No. 636,285, Dec. 31, 1990, Pat. No. 5,090,424.

[51] Int. Cl.$^6$ ............................ A61F 5/48; A61F 2/00
[52] U.S. Cl. ............................ 128/885; 128/DIG. 25; 600/29
[58] Field of Search .................... 128/846, 885, 128/DIG. 25; 600/29–31

[56] References Cited

U.S. PATENT DOCUMENTS

| | | | |
|---|---|---|---|
| 1,887,526 | 11/1932 | Spielberg | 604/287 |
| 2,494,393 | 1/1950 | Lamson | 128/1 |
| 2,638,093 | 5/1953 | Kulick . | |
| 3,646,929 | 3/1972 | Bonnar | 128/1 |
| 3,789,828 | 2/1974 | Schulte . | |
| 3,797,478 | 3/1974 | Walsh et al. . | |
| 3,841,304 | 10/1974 | Jones . | |
| 4,019,499 | 4/1977 | Fitzgerald . | |
| 4,209,009 | 6/1980 | Hennig | 600/30 |
| 4,258,704 | 3/1981 | Hill | 600/32 |
| 4,428,365 | 1/1984 | Hakky | 128/1 |
| 4,457,299 | 7/1984 | Cornwell . | |
| 4,553,533 | 11/1985 | Leighton . | |
| 4,682,592 | 7/1987 | Thoregard | 128/303 R |
| 4,846,784 | 7/1989 | Haber | 600/29 |
| 4,850,963 | 7/1989 | Sparks et al. | 600/29 |
| 4,938,759 | 7/1990 | Enscore et al. | 604/896.1 |
| 4,946,449 | 8/1990 | Davis, Jr. | 604/256 |
| 4,981,465 | 1/1991 | Ballan | 600/32 |
| 5,090,424 | 2/1992 | Simon et al. | 128/885 |
| 5,114,380 | 5/1992 | Larsen | 452/176 |
| 5,114,398 | 5/1992 | Trick et al. | 604/29 |
| 5,116,387 | 5/1992 | Berg | 623/66 |

FOREIGN PATENT DOCUMENTS

| | | | |
|---|---|---|---|
| 8810106 | 12/1988 | WIPO | A61F 2/48 |
| 8900030 | 1/1989 | WIPO | A61B 19/00 |

OTHER PUBLICATIONS

Nielsen et al., "The Urethral Plug: A New Treatment Modality for Genuine Urinary Stress Incontinence in Women", Nov. 1990, pp. 1199–1202 Journal of Urology, vol. 144.

*Primary Examiner*—Michael A. Brown
*Attorney, Agent, or Firm*—Lorusso & Loud

[57] ABSTRACT

A device for the control of urinary incontinence comprising a urethral plug self-movable between a first condition in which the plug is relatively rigid and generally tubular, with a smaller diameter for travel through the orifice of the urethra, and a second condition in which the plug is flexible and expansible to a larger diameter for retaining the plug in a mammalian body and blocking the flow of urine. A larger diameter is achieved by exposure of a tube-like member of the plug to natural bodily conditions, resulting in an automatic expansion of the tube, whereupon the expansion causes the tube-like member to form a seal with the urethra, bladder neck or bladder wall. The plug further has a meatal plate for anchoring the plug in the urethra and preventing migration into the bladder. Removal of the plug for bladder evacuation is easily accomplished by grasping and pulling a tab associated with the meatal plate, or in another embodiment by pulling on a cord means associated with the meatal plate, causing the deformation of the expanded tube to a smaller diameter. In accordance with a further feature of the invention, there is provided a method for controlling incontinence in mammals.

35 Claims, 3 Drawing Sheets

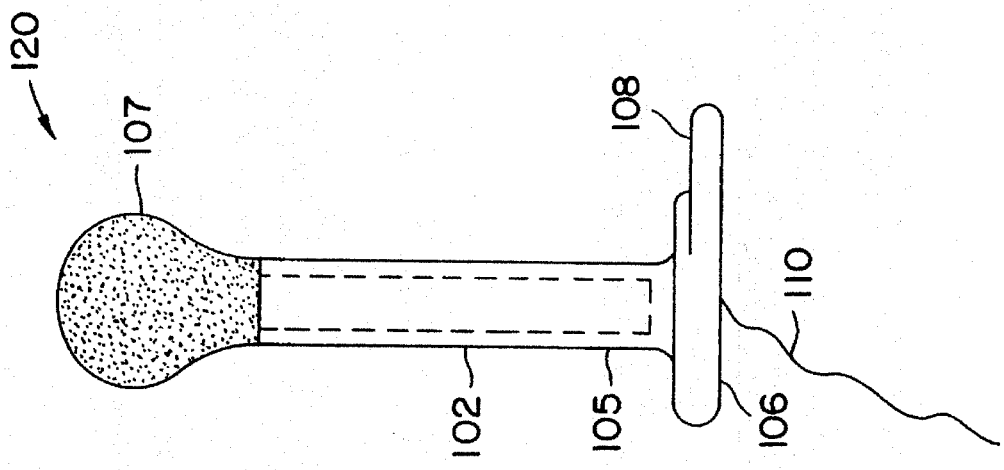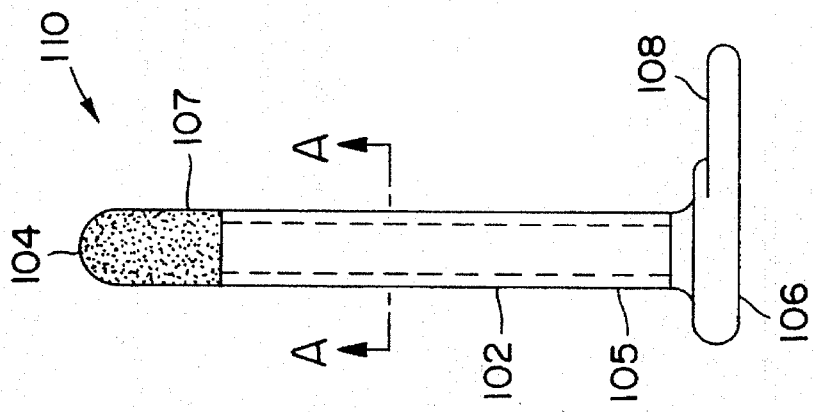

EXPANDABLE URETHRAL PLUG

CROSS REFERENCE TO A RELATED APPLICATION

This is a continuation of application Ser. No. 08/088,469, filed on Jul. 7, 1993, now abandoned, which is a continuation-in-part application of prior application U.S. Ser. No. 811,571, filed Dec. 20, 1991, which is a continuation-in-part application of application U.S. Ser. No. 746,364, filed Aug. 16, 1991, now abandoned, which is a continuation-in-part application of U.S. Ser. No. 636,285, filed Dec. 31, 1990, now U.S. Pat. No. 5,090,424.

FIELD OF THE INVENTION

The present invention relates generally to the control of urinary incontinence and is directed particularly to an expandable, removable urethral plug for the prevention of urinary incontinence.

BACKGROUND OF THE INVENTION

Urinary stress incontinence is defined as the involuntary loss of urine when the pressure within the bladder exceeds the maximum urethral pressure in the absence of detrusor activity. While the problem of urinary incontinence occurs in men and women, it is an affliction especially common in women of child bearing age and beyond.

There are in existence many methods used to address the problem of incontinence, ranging from surgery on the bladder to insertion of urine drainage devices. Bladder neck suspension surgery, wherein the neck of the bladder is reduced by suspending the bladder, has been a preferred method of treating incontinence, especially in younger patients. However, there are numerous risks associated with such surgery, notwithstanding the expense. For some patients, surgery is not recommended for medical or other reasons, and for those with mild incontinence surgery is not an appropriate solution.

Early attempts to solve the problem of urinary incontinence without permanent alteration to the bladder included surgically implanted, non-manipulable indwelling devices. Research efforts continued to seek improvements to these non-manipulable devices and devised a surgically implanted, manipulable indwelling device, thus affording the wearer some control over bladder evacuation. Further efforts to improve urinary blocking devices centered on indwelling devices that did not require surgical implantation. Of this type, two kinds exist: those indwelling devices requiring insertion and/or fitting by a health care professional and those more simple, indwelling devices which can be inserted by the wearer. Further research has expanded on the non-surgically implanted devices and has resulted in a device capable of being removed by the wearer for voiding and then reinserted upon completion. This type of device relies on fluid or gel for operation. Examples of the prior art procedures and/or devices will now be briefly discussed.

There are in existence a variety of devices for controlling urinary incontinence. Many of these devices require surgery for implantation, and of these surgically implanted devices, there are two distinct types: non-manipulable devices and manipulable devices. One such non-manipulable device, described in U.S. Pat. No. 4,019,499, is a capsule filled with a variable amount of fluid. The capsule is surgically implanted between supporting tissue and the urethra to exert an occluding force thereon. A similar, non-manipulable capsule implant is described in U.S. Pat. No. 3,789,828. However, this device has ties extending therefrom to aid in fiber ingrowth, thus providing mechanical stability to the capsule. One problem associated with this device is the risk of fluid leakage. In addition to problems with leakage, severe tissue damage may result from the unnatural method in which such devices regulate incontinence.

Other surgically implanted devices exist which are manipulable in style. These devices provide the wearer with the ability to selectively control the operation of the device via manually operable elements implanted in the tissue surrounding the urethra. U.S. Pat. Nos. 4,428,365, and 4,846,784 each disclose an indwelling device having an inflatable chamber with an attached tubing and an inflation bulb. The wearer may manually adjust the pressure exhibited by the inflatable member on the urethra, simply by squeezing the tissue encasing the bulb. These devices, however, often produce thickening and scarring of surrounding tissue, making their usefulness questionable. Additional adverse effects associated with surgically implanted indwelling devices, whether non-manipulable or manipulable in nature, are encrustation, irritation and infection. Also, surgery subjects the patient to a number of hazards, such as post-operative bleeding, bladder spasm, and urinary infection, not to mention the risks associated with anesthesia and the significant pain, anxiety and inconvenience inherent in any surgical procedure.

There are also known in the art certain indwelling devices that do not require surgical implantation. These devices are inserted by a physician through the urethral orifice and allow the wearer to void either past or through the device. An example of such a device is disclosed in U.S. Pat. No. 4,850,963 in which a physician inserts a bolus of ferromagnetic material through the urethra and into the bladder. The bolus rests at the juncture of the bladder and urethra and is moved for bladder evacuation, by the relative positioning of a magnet across the body of the wearer. However, the bolus may become lodged in an area beyond the reaches of the magnetic force exhibited by the magnet, making the device inoperative. And, as with any indwelling device, there is always a significant risk of infection as well as leakage and rupture over time. Another example of this type of indwelling device is the pre-stressed capsule disclosed in U.S. Pat. No. 4,457,299. The capsule is inserted by a physician within the lower interior of the urethra and is set at a pre-stressed pressure slightly above involuntary pressure. When the urine pressure exceeds the pre-set pressure of the capsule, the capsule deforms allowing urine to flow around the device. This device, however, has no feature to prevent migration of the device into the bladder or out of the urethra. In U.S. Pat. No. 4,553,533, there is shown a prosthetic urethral sphincter valve which is placed in the urethra and anchored in the bladder. The patient increases his bladder pressure by means of a valsalva maneuver, and holds this pressure while the valve activates. Urine may then pass through the valve with the valve later returning to its closed position. This device is very complicated, expensive, difficult to manufacture and uncomfortable. While these devices do not require surgical implantation, they nonetheless require a physiciany's time and technique for insertion. And more importantly, these devices, being indwelling during the entire voiding cycle, are often cumbersome to the wearer while inviting numerous complications such as encrustation, irritation and infection.

Additional devices exist that are adapted to be inserted by a physician into the urethra and remain indwelling through several voiding cycles. U.S. Pat. No. 3,797,478 discloses a device having an expandable collar which is inflated after insertion, by an injection of fluid therein. The patient voids through this device while it remains indwelling. When it is desired to remove the device, the inflated collar is ruptured or serrated by inserting a pin or other cutting instrument, thus expelling the fluid into the wearer's body. In addition to the cumbrous use of this device, a risk of infection is associated with the release of injection fluid upon removal. Similarly, U.S. Pat. No. 3,841,304 discloses a plug which is inserted into the urethra by a physician and subsequently inflated to block the flow of urine. This device may be left in the body for extended periods. After insertion, the device requires repositioning in the urethra to permit bladder evacuation. The wearer voids around the device as it remains indwelling. Such a device leaves the wearer susceptible to infection, as bacteria may be introduced into the urethra during repositioning, or during indwelling time. Also, serious complications can occur upon removal, when a separate wire must be inserted therein.

Also known in the art are devices capable of being inserted by the wearer into the urethra and removed from the urethra by the wearer for voiding. Upon completion of bladder evacuation, the wearer reintroduces the plug into the urethra. One such example comprises a solid-type urethral plug adapted to be inserted by the wearer. It is described by Neilsen, Kurt K. et al., in "The Urethral Plug: A New Treatment Modality for Genuine Urinary Stress Incontinence in Women", *J. Urology*, vol. 44, p. 1100 (1990). This device consists of one or two solid spheres located along a soft shaft, and a thin, soft plate located at the end of the shaft. One sphere is located upstream of the maximum urethral closing pressure point, corresponding to the location of the sphincter. In the two sphere embodiment, the second sphere is located with its midpoint at the bladder neck, and is used to assist in reducing urinary flow and pressure transmission to the urethra so that the sphincter can operate. When the patient wants to evacuate the bladder, the plug is removed, evacuation occurs, and a fresh plug is inserted. One problem associated with this device is that the patient must have three urethral closure pressure profiles performed as well as other examinations, before the device is made for the wearer. Additional problems associated with this device include placement difficulties, lack of sealing capabilities associated therewith, inadequate retention, therefore allowing expelling, and inadequate anchoring by the plate at the meatus. In addition to such problems is the discomfort associated with insertion and removal, due to the size profile and rigidity of the spheres, which maintain a constant diameter during insertion and removal.

Another "remove-to-void" device is disclosed in U.S. Pat. No. 5,090,424, which comprises a conformable urethral plug. The body of the plug forms a cavity which is in fluid communication with another cavity via a check-valve. Thus, fluid may be pumped into the cavity within the urethra to provide a custom fit. This device, like many others relying on liquids or gels for expansion, relies heavily on a fluid-tight valve in order to maintain retention. Should valve failure occur, evacuation would immediately follow. It also requires some degree of user actuation in that the wearer must squeeze on a portion of the device to move the fluid through the check valve and into the body of the plug for expansion thereof. This may be difficult for some patients, especially the elderly and/or those weakened by illness. There is also a chance of fluid leakage into the body of the wearer should rupture of the plug occur.

As shown above, conventional devices for controlling urinary incontinence have many disadvantages associated therewith. Indwelling devices often lead to tissue damage and infection. Others are uncomfortable, cumbersome, leaky and often migratory. No prior art, either alone or in combination, has been shown to disclose a device for controlling urinary incontinence which is easily insertable and removable by the wearer for bladder evacuation and which, upon insertion into the urethra, is adapted to expand without the use of air, fluid, gel, or other means to a diameter which effectively forms a seal with the urethral, bladder neck or bladder wall.

SUMMARY OF THE INVENTION

Accordingly, one object of the present invention is to provide a urethral plug which is easily manipulated by the wearer.

It is another object of the present invention to provide a urethral plug which is inserted into the urethra of a subject wherein it automatically and without user intervention expands to form a seal with the urethra, bladder neck or bladder wall and block the flow of urine, after which it is removed by the subject.

Another object of the present invention is to improve the degree of comfort associated with insertion and removal of a urethral plug.

A further object of the present invention is to enhance the sealing ability of a urethral plug with the urethra, bladder neck or bladder wall.

Another object of the present invention is to stabilize the placement of a urethral plug at the urethral meatus, such that migration into the bladder will not occur.

Another object of the present invention is to reduce the risk of contamination to the wearer of a urethral plug.

Still another object of the present invention is to provide a method of using a urethral plug by patients suffering from urinary incontinence.

It is yet another object of the present invention to provide a method of using a removable-to-void urethral plug which expands automatically without user intervention for retention in the body and to block the flow of urine in the urethra.

With the above and other objects in view, as will hereinafter appear, the present invention provides a novel urethral plug comprising a member possessing a contracted diameter for easy insertion and removal through the orifice of the urethra, and a larger, expanded diameter for retaining the plug in the urethra and blocking the flow of urine. A larger diameter is achieved by providing a urethral plug adapted to assume a non-expanded first condition when exposed to a temperature approximately less than that of a mammalian body, and adapted to assume an expanded second condition when exposed to a transition temperature of approximately the body temperature of a mammal. In another embodiment, the expanded second condition is achieved when the urethral plug is exposed to natural bodily conditions such as, but not limited to, body moisture. The adaptation of the plug to the expanded second condition occurs automatically without actuation by the user of the plug. The plug in the first condition may be relatively rigid and substantially tubular in configuration, being shaped and sized for easy insertion through the orifice of the urethra. In the second condition, the plug is flexible and capable of expanding to a size substantially greater in diameter than the size of the plug in the first condition, due to diametric expansion of the member. The diametric expansion of the proximal part of the member causes the plug to expand, thus sealing the plug to the urethra, bladder neck or bladder wall. The seal thus created serves to retain the plug in the urethra, bladder neck or bladder while blocking the flow of urine.

The urethral plug of the present invention further has a meatal plate for anchoring the plug at the urethral meatus and preventing migration of the plug into the bladder. Removal of the plug, for bladder evacuation, is easily accomplished by a continuous tug on a tab associated with the meatal plate.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

FIG. 3 shows a second embodiment of the urethral plug of the present invention having a coated tip of hydrophillic material, in its contracted configuration.

FIG. 4 shows a second embodiment of the urethral plug of the present invention in its expanded configuration.

DETAILED DESCRIPTION OF THE INVENTION

Figure 2:
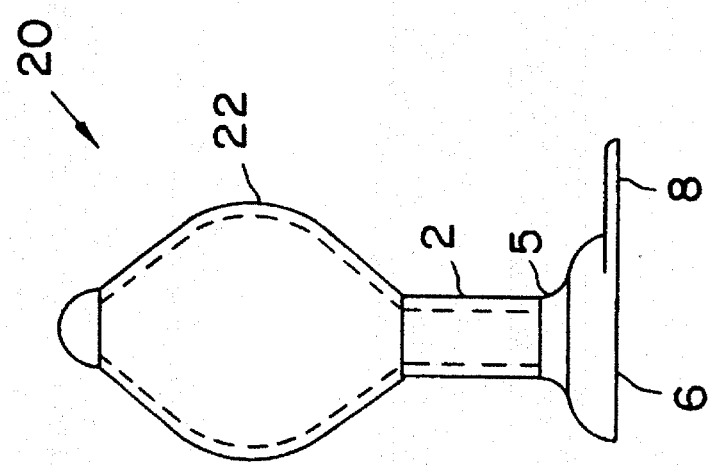
FIG. 2 shows the urethral plug of the present invention in its expanded configuration.

At the outset, the invention is described in its broadest overall aspects with a more detailed description following.

In its broadest embodiment, the present invention is a device for treatment of incontinence in males and females and a method for using the device to stop unwanted flow of urine.

The device of the broadest embodiment is adaptable to conform to the specific physical and physiological characteristics of the urethra. The device is intended for use in the management and treatment of urinary incontinence and designed to cause blockage of the urethra, bladder neck or bladder. While this invention may be used for any type of urinary incontinence, it is particularly useful for stress incontinence.

The device is comprised of a temperature sensitive compound, more particularly a plastic polymer compound, even more particularly, a polyurethane-based polymer compound. The compound is selected for its expansion properties when subjected to temperatures of up to about and including 37° C., which temperatures encompass the range of temperature of a mammalian body, more particularly, a human body. The compound further exhibits properties of shape memory.

The urethral plug of the present invention is formed from a mold having a hollow center. The shape memory polymer material is blow molded into the maximum expanded shape desired for the plug. For purposes of this application, this maximum expanded shape is the "mold shape plug". The "mold shape plug" is drawn through a tubular shaped die heated beyond the transition temperature of the shape memory polymer material, thereby reducing the diameter of the "mold shape plug" to form a tubular shape, hereinafter referred to as the "pre-insertion plug". Immediately after withdrawing the plug from the die, it is cooled to a temperature below the transition temperature of the shape memory polymer material to maintain its "pre-insertion plug" shape. This process produces a plug suitable for insertion into a subject's urethra.

The plug is now ready for packaging. Packaging means includes encasing the "pre-insertion plug" in a suitable plastic molded tray designed to maintain the "pre-insertion plug" diameter during shipping, handling and temperature fluctuations above the transition temperature of the shape memory polymer material. Encasing the "pre-insertion plug" in a gelatin material will also maintain the "pre-insertion plug" diameter while the plug is in storage or transit. For those plugs packaged in gelatin, the gelatin simply dissolves when exposed to moisture in the body when inserted by the subject.

Upon insertion of the plug into the urethra of a mammal, the plug is exposed to a temperature gradient which triggers automatic expansion of the device. Remembering the "mold shape plug", the plug begins to expand from its pre-insertion shape to the shape of its "mold shape plug." As it expands toward this end, the plug conforms to the shape and size of the urethra, especially upstream of the sphincter toward the bladder neck. The plug continues to expand diametrically as it continues to realize the shape of its "mold shape plug", with the outer limits of expansion defined by the walls of the urethra. Under no circumstances, however, can the plug expand beyond the dimensions of the "mold shape plug". The shape memory polymer comprising the plug is only capable of expanding and conforming to the environment into which it is placed; it is incapable of exerting a resistive force by itself.

There is no need to custom make the plug for each individual; the subject's urethra is simply measured by a physician to ensure that the proper length and size plug is used. The plug may be manufactured in several lengths and sizes in order to accommodate males and females, adults and children. In its active and operational state, and when properly sized and used, the plug forms a secure seal with the urethral, bladder neck or bladder wall. The flow of urine through the urethra is thus blocked.

Figure 1:
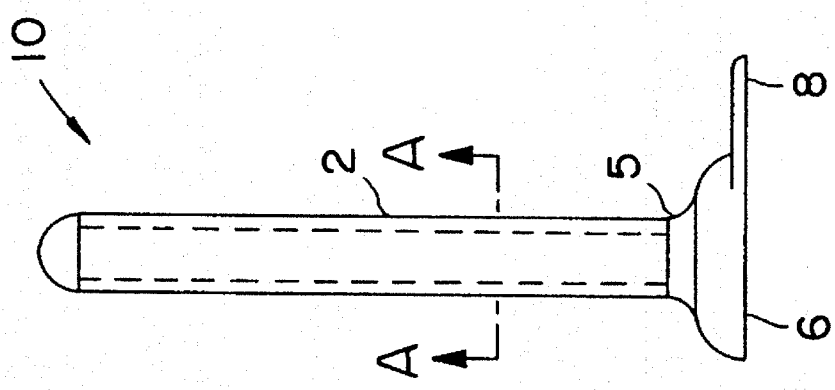
FIG. 1 shows the urethral plug of the present invention, which has an expandable member, in its contracted configuration.

FIG. 1 shows the urethral plug in its contracted configuration 10. Tube 2 is a hollow, thin-walled cylindrical tube which is sized to be easily inserted through the orifice of the urethra. The tube 2 is made from a biocompatible material having characteristics of expansion and compressibility. At the distal end 5 of the tube 2 is a meatal plate 6. The meatal plate 6 is a flanged-type member which is adapted to anchor the urethral plug at the meatus urinarius. To carry out this function of anchoring, the meatal plate 6 is of a thickness sufficient to withstand bodily compression during wear, preferably on the order of 1 millimeter or greater. The meatal plate 6 will prevent the plug from passing through the orifice of the urethra and into the proximal urethra, bladder neck or bladder.

Figure 5:
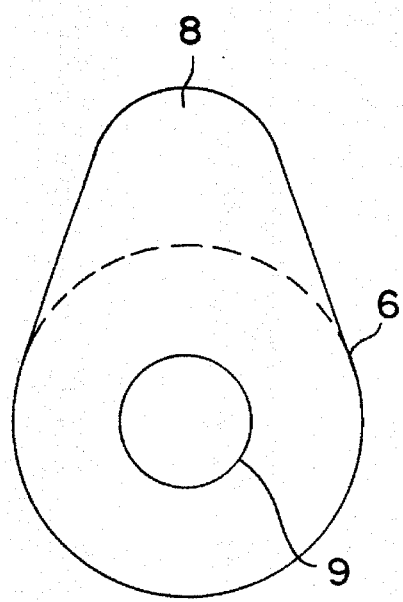
FIG. 5 shows a perspective view of the meatal plate of the urethral plug of the first and second embodiments.

FIG. 5 shows a bottom perspective view of the meatal plate 6 in FIG. 1, which is the same as meatal plate 106 in FIG. 3. A portion of the meatal plate 6 is extended so as to form a tab 8, which tab may be grasped by the wearer for ease of removal. The meatal plate has an opening 9 therein lying within the plane of the opening of the tube 2.

Referring again to FIG. 1, the tube 2 is preferably formed of a biocompatible thermoplastic material. In a preferred embodiment, the tube 2 is made of a known polyurethane-based polymer which provides the plug with shape memory. The unique characteristic of the plastic polymer is its thermally triggered shape memory, which allows the tube 2 constructed of the shape memory polymer to be inserted into the urethra in a relatively compressed and elongated state, and regain a useful shape at a selected temperature, such as human body temperature. The two interchangeable shapes are possible because the shape memory polymer has "elastic memory" that is a large reversible change in elastic modulus across the glass transition temperature (Tg). Thus, the shape memory polymer offers the unique characteristic of changing from a glassy, more rigid condition to a softer, rubbery condition across the Tg temperature. Such a large change in elastic modulus around the Tg temperature allows for significant deformation in response to temperature changes. An increase in temperature allows the shape memory polymer to become more flexible and, therefore, easily deformable into a new shape. The glass transition of a polymer, such as the shape memory polymer of the preferred embodiment, is depicted below.

Any compound with thermally-triggered shape memory and having a glass transition temperature approximately that of mammalian body temperature can be used in the device of the present invention. A preferred compound is the polyurethane-based shape memory polymer as described above, developed by Mitsubishi Heavy Industries, Ltd. and available from Memry Technologies in Brookfield, Conn.

Line A—A in FIGS. 1 and 3 represents the cross sectional view of the tubes 2 and 102, respectively, which will be discussed further in FIGS. 6A and 6B.

Accordingly, when the urethral plug shown in FIG. 1 is subjected to a transition temperature, the relatively rigid plug changes to a second condition in which it is flexible and easily deformable. The plug is now pliable and, remembering its "mold shape plug", able to expand significantly in diameter to conform to the shape of the wearer's urethra. A tight seal with the urethra, bladder neck or bladder wall is formed and the plug is retained in the wearer's urethra to block the flow of urine.

In accordance with the above discussion, the user inserts the urethral plug of the present invention into the urethra while it is in the configuration of FIG. 1. Once the plug has been inserted into the urethra and the meatal plate 6 abuts the meatus urinarius, the plug is exposed to the heightened temperature of the human body. The temperature increase causes the shape memory polymer comprising the tube 2 to automatically expand outwardly and achieve a protrusion 22 to conform to the size and shape of the wearer's urethra. The shape memory polymer is able to freely adapt and conform to its environment—here, the urethra—because, as already discussed, it is only capable of expanding and conforming to the environment into which it is placed; it is incapable of exerting a resistive force by itself. This important characteristic of the shape memory polymer prevents displacement of the urethra, bladder neck or bladder by the shape memory polymer material.

The plug is now in its expanded configuration 20 as set forth in FIG. 2. As urine accumulates in the bladder, pressure from the accumulating urine builds until the bladder is sufficiently full to exert a downward force on the urine in the bladder neck and urethra. The downward force in turn bears down on the proximal portion of the expanded member of the plug, furthering the diametrical expansion of the proximal portion of the member. The expansion of the plug, in its expanded form, provides a tight seal with the wall of the urethra, bladder neck or bladder to retain the plug in the wearer's body. When the wearer wishes to remove the plug to void, a continuous tug on tab 8 of the meatal plate 6 will cause the rubbery, diametrically expanded member to elongate. The tube 2 is then returned to a smaller diameter and is simply withdrawn from the body. Other means for removal of the plug is contemplated, such as but not limited to, a pulling means, such as a cord, whereby the plug is simply removed by pulling on a cord attached to the plug. The ease with which the shape memory polymer plug allows removal prevents discomfort potentially associated with plug removal.

FIG. 3 shows a second embodiment of the automatically expandable urethral plug of the present invention in its contracted 110 configuration. Similar to the first embodiment discussed above, tube 102 comprises a hollow, thin-walled cylindrical shaft which is sized to be easily inserted through the orifice of the urethra. In an alternative embodiment, the tube 102 may comprise a solid cylindrical shaft. The tube 102 may be made of any inert material suitable for insertion into a mammalian body. The tube 102 is made from a biocompatible material, preferably from a biocompatible thermoplastic elastomer, more preferably from a biocompatible polyurethane-based polymer. The most preferred tube is injection molded Kraton G, a non-toxic, biocompatible thermoplastic elastomer. Other suitable materials include polyethylene and nylon polymers, and other copolymers similar thereto.

At the proximal end 104 of tube 102, there is an expandable, deformable member 107 which, upon insertion into a mammalian body, is exposed to normal bodily conditions. Exposure to the normal bodily conditions in turn causes the member 107 to expand and achieve its expanded 120 configuration, as shown in FIG. 4. The member 107 may be sponge or any suitable absorbent hydrophillic material. The expandable, deformable member 107 may be attached to the tube 102 by an adhesive, a collar, thermal bonding, or any attaching means suitable for the materials selected for the member 107. The bodily conditions which affect the member 107 are temperature (as in the shape memory material device); moisture; pH gradations; and/or other such conditions that act on and expand the member 107.

At the distal end 105 of the tube 102 is a meatal plate 106 which, as in the aforementioned embodiment, is a flanged-type member with a thickness sufficient to prevent compression by the urethra during insertion and wear, preferably on the order of 1 millimeter or greater. Additionally on the meatal plate is a tab 108 for ease of removal. Tab 108 is instructive only and can be substituted by other removal means such as, but not limited to, a cord 110 (FIG. 4) attached to the inside of the tube 102 and extending downwardly through the opening 9 in the meatal plate. Any other such adaptation sufficient to allow removal of the device by a simple, continuous pulling by the subject, without tools or undue force, is equally contemplated.

The expandable, deformable member 107 has a pre-insertion shape which is sufficiently sized to allow easy insertion into the urethra of a mammalian body, more particularly, a human body. Once inserted, natural conditions in the body cause expansion, preferably diametrical expansion, of the member 107. In one embodiment, the member would be a sponge secured to the tube 102 by any of, but not limited to, the aforementioned attaching means. Upon insertion of the plug into the body, the sponge is exposed to and absorbs moisture naturally present in the body and expands diametrically, thereby forming a secure seal with the urethral, bladder neck or bladder wall of the body. As in the urethral plug comprised of the shape memory polymer material, the urethral plug of this embodiment also expands diametrically until it meets with resistance from the walls of the urethra, bladder neck or bladder. It can exert no resistive force of its own and, therefore, is incapable of displacing the urethra, bladder neck or bladder of the wearer. The member 107 maintains its expanded state until acted upon by the wearer, for instance, when voiding is desired. The diametrically expanded member is sufficiently soft and deformable so as to respond to the downward pressure exerted by the wearer's pulling on the tab 108 or other pulling means. A continuous tug on tab 108 of the meatal plate 106, or on cord 110, will cause the expanded member 107 to elongate. The plug is then returned to a smaller diameter and is simply withdrawn from the body.

Figure 6A:
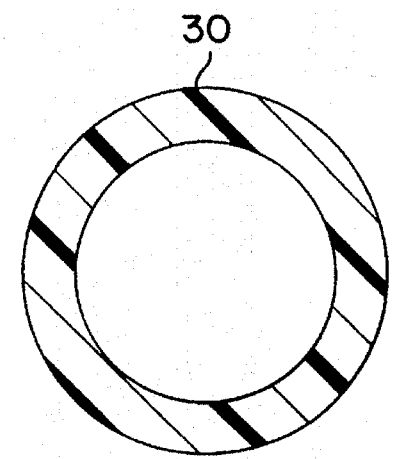
FIG. 6A shows a cross sectional view of the urethral plug of the first and second embodiments, taken along line A—A of FIGS. 1 and 3.
Figure 6B:
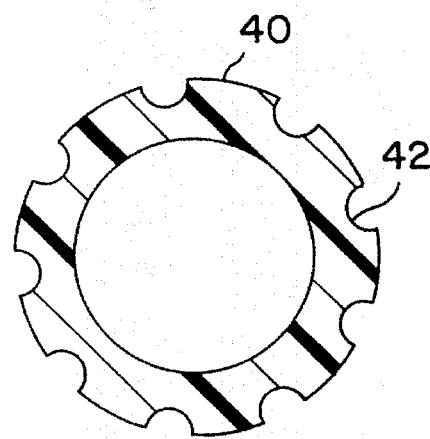
FIG. 6B is similar to FIG. 6A, but shows a cross sectional view of an alternate embodiment of the urethral plug of the present invention.

FIG. 6A shows a cross sectional view of the urethral plug along line A—A of the preferred embodiments set forth above. Tube 30 represents the diameter of tube 2 of FIG. 1 and tube 102 of FIG. 3. FIG. 6B shows an alternative embodiment, along line A—A, of the tube 2 of FIG. 1 and the tube 102 in FIG. 3 in cross section. As shown in FIG. 6B, the diameter of tube 40 is not constant but variant as shown by the radiused grooves 42 extending longitudinally along the tube diameter. The radiused grooves 42 provide increased surface area contact which improves the coaptive interaction of the tube with the urethra. Such enhanced sealing ability of the plug means a better fit for the wearer.

The claimed invention provides a novel urethral plug which may be comfortably inserted into, worn in, and removed from the urethra, due to its ability to expand from a smaller to a larger diameter for operation in the urethra, and deform to the smaller diameter for removal. Additionally, the shape memory material comprising the plug of the first embodiment and the hydrophillic material comprising the member portion of the plug of the second embodiment, provide enhanced sealing of the urethra, bladder neck or bladder, making leakage of urine unlikely. Moreover, the plug, being equipped with a meatal plate, will not migrate into the bladder, causing complications. Lastly, the plug is easily removed for bladder evacuation. The wearer then simply inserts a fresh plug and is again afforded control of urinary incontinence.

While the invention has been particularly shown and described with reference to the aforementioned embodiments, it will be understood by those skilled in the art that various changes in form, composition and detail may be made therein without departing from the spirit and scope of the invention. Thus, any modification of the shape, configuration and/or composition of the elements comprising the invention is within the scope of the present invention.

What is claimed is:

1. A remove-to-void device for blocking unwanted flow of urine comprising an expandable member, said member comprising a plastic polymer processing a first shape prior to insertion into a human body said first shape being insufficient in size and volume to form a plug to block the flow of urine and a second shape following insertion into said human body, said second shape being in response to the environment of the urethra, bladder neck or bladder, said second shape forming a urine-impermeable plug, said urine-impermeable plug being of sufficient size and volume so as to remain in place against the flow of urine said second shape occuring automatically without user intervention, such that in said first shape said member is adapted to be configured in its non-expanded disposition, and in said second shape said member is adapted to be configured in its expanded disposition.

2. The device of claim 1, wherein said member further comprises a meatal plate.

3. The device of claim 2, wherein said meatal plate has a thickness sufficient to withstand compression by the urethra of said human.

4. The device of claim 3, wherein said thickness is at least 1 millimeter or greater.

5. The device of claim 1, wherein said device is inserted into said human body through a urethral meatus.

6. The device of claim 1, wherein said member in said second shape conforms to the shape of said human's urethra, bladder neck or bladder.

7. The device of claim 1, wherein said member is comprised of a compound which, prior to insertion of said device into the human body, indefinitely retains said first shape, and which, following insertion of said device into the human body, automatically without user intervention assumes said second shape in which said member is greatly expanded relative to said first shape.

8. The device of claim 1, wherein said plastic polymer comprises polyurethane.

9. The device of claim 1, wherein said member is round in cross-section.

10. The device of claim 1, wherein said member further comprises radiused grooves in cross-section.

11. The device of claim 1, further comprising means for removal of said device.

12. The device of claim 11, wherein said means for removal is a tab.

13. The device of claim 11, wherein said means for removal is a cord.

14. A remove-to-void device for use in the urethra to control urinary incontinence comprising an expandable member, said member comprising a plastic polymer and being adapted to assume a first condition in which said member is relatively rigid and substantially tubular in configuration, said first condition being insufficient in size and volume to form a plug to block the flow of urine, said member being further adapted to assume a second condition in which said member becomes flexible and expandable in response to the environment of the urethra, bladder neck or bladder, said second condition forming a urine-impermeable plug, said urine-impermeable plug being of sufficient size and volume so as to remain in place against the walls of the urethra, bladder neck or bladder while blocking the flow of urine, wherein said first condition exists prior to insertion of said device into a human body and said second condition exists automatically without user intervention following insertion of said device into the human body, the device further comprising a cord attached to said member, which when pulled by a wearer, allows said plug to be removed so that the wearer can void.

15. The device of claim 14, wherein said member further comprises a meatal plate.

16. The device of claim 15, wherein said meatal plate has a thickness sufficient to withstand compression by the urethra.

17. The device of claim 16, wherein said thickness is at least 1 millimeter or greater.

18. The device of claim 14, wherein said device is inserted into said human body through a urethral meatus.

19. The device of claim 14, wherein said member in said second condition conforms to the shape of said human body's urethra, bladder neck or bladder.

20. The device of claim 14, wherein said member is comprised of a compound which in said first condition, prior to insertion of said device into the human body, indefinitely retains said rigidity and said tubular configuration, and which, following insertion of said device into the human body, assumes automatically without user intervention said second condition in which said member is greatly expanded relative to said first condition.

21. The device of claim 14, wherein said plastic polymer comprises polyurethane.

22. The device of claim 14, wherein said member is round in crosssection.

23. The device of claim 14, wherein said member further comprises radiused grooves in cross-section.

24. The device of claim 14, further comprising means for removal of said device.

25. The device of claim 24, wherein said removal means is a tab.

26. An automatically expanding, remove-to-void device for blocking unwanted flow of urine comprising a shaft substantially tubular in configuration having an expandable, deformable member at the proximal end of said shaft, said member comprising a plastic polymer and possessing a first shape prior to insertion into a human body, said first shape being insufficient in size and volume to form a plug to block the flow of urine, and a second shape following exposure to bodily conditions in the environment of the urethra, bladder neck or bladder after insertion therein, said second shape forming a urine-impermeable plug, said urine-impermeable plug being of sufficient size and volume so as remain in place against the walls of the urethra, bladder neck or bladder while blocking the flow of urine, said second shape occurring automatically without user intervention, the device further comprising a cord attached to said shaft, which when pulled, allows a wearer to remove the device to void.

27. The device of claim 26, wherein said shaft further comprises a meatal plate.

28. The device of claim 27, wherein said meatal plate has a thickness sufficient to withstand compression by the urethra of said human body.

29. The device of claim 28, wherein said thickness is at least 1 millimeter or greater.

30. The device of claim 26, wherein said shaft is made of a biocompatible plastic polymer.

31. The device of claim 30, wherein said biocompatible plastic polymer is selected from the group consisting of thermoplastic elastomers, polyethylene polymers, polyurethane polymers, and nylon polymers.

32. The device of claim 26, further comprising means for removal of said device.

33. The device of claim 32, wherein said removal means is a tab.

34. A method for preventing an unwanted discharge of urine comprising the following steps:

(a) providing a remove-to-void expandable plug comprising a plastic polymer which can be inserted into a urethra, bladder neck or bladder of a human;

(b) inserting the remove-to-void expandable plug into the urethra, bladder neck or bladder of the human while the plug is in a first shape, said first shape being insufficient in size and volume to form a urine-impermeable barrier to the flow of urine;

(c) maintaining the plug in the urethra, bladder neck or bladder to allow expansion of the plug to form a second shape in response to the environment within the urethra, bladder neck or bladder, said second shaped being of sufficient size and volume to form a urine-impermeable barrier to the flow of urine, said second shape thereby retaining the plug in the urethra, bladder neck or bladder and restricting the flow of urine from the bladder through the urethra, said second shape occurring automatically without user intervention; and (d) removing the plug from the urethra, bladder neck or bladder to discharge the urine, by pulling on a cord attached to said plug, which discharge could not be accomplished without removing said plug.

35. A method for preventing an unwanted discharge of urine comprising the following steps:

(a) providing a remove-to-void device including an expandable member comprising a plastic polymer which can be inserted into the urethra, bladder neck or bladder of a human;

(b) inserting the remove-to-void device into the urethra, bladder neck or bladder of the human while the expandable member is in a first shape, said first shape being insufficient in size and volume to form a urine-impermeable barrier to the flow of urine;

(c) maintaining the remove-to-void device in the urethra, bladder neck or bladder to allow expansion automatically without user intervention of the member to form a second shape in response to the environment within the urethra, bladder neck or bladder, said second shape being of sufficient size and volume to form a urine-impermeable barrier to the flow of urine, said second shape, thereby retaining the device in the urethra, bladder neck or bladder and restricting the flow of urine from the bladder through the urethra; and (d) removing the device from the urethra, bladder neck or bladder to discharge the urine, which discharge could not be accomplished without said removing of said plug.

* * * * *

UNITED STATES PATENT AND TRADEMARK OFFICE
CERTIFICATE OF CORRECTION

PATENT NO.   : 5,513,660
DATED        : May 7, 1996
INVENTOR(S)  : Simon, et al.

It is certified that error appears in the above-indentified patent and that said Letters Patent is hereby corrected as shown below:

Column 2, Line 59:   Delete "physicany's" and insert -- physician's -- therefor;

Column 4, Line 51:   Delete ".expanded" and insert -- expanded -- therefor;

Signed and Sealed this

Eighth Day of October, 1996

Attest:

BRUCE LEHMAN

Attesting Officer    Commissioner of Patents and Trademarks